United States Patent [19]

Diamond et al.

[11] Patent Number: 5,069,895
[45] Date of Patent: Dec. 3, 1991

[54] METHODS FOR THE TREATMENT OF ALCOHOL INTOXICATION AND DEPENDENCE

[76] Inventors: Ivan F. Diamond, 761 San Diego Rd., Berkeley; Adrienne S. Gordon, 23 Norwood Ave., Kensington, both of Calif. 94707

[21] Appl. No.: 434,066

[22] Filed: Nov. 9, 1989

[51] Int. Cl.$^5$ ............................................. A61K 49/00
[52] U.S. Cl. ....................................... 424/10; 514/46; 514/258; 514/259; 514/387; 514/811
[58] Field of Search .................. 424/10; 514/258, 259, 514/387, 811, 46

[56] References Cited

PUBLICATIONS

Chemical Abstracts (106: 67250g) 1987.
Chemical Abstracts (106: 149316x) 1987.
Chemical Abstracts (112: 30385c) 1989.
Nagy et al. (1988) Proc. Natl. Acad. Sci. U.S.A. 85:6973–6976.
Gordon et al. (1986) Proc. Natl. Acad. Sci. U.S.A. 83:2105–2108.
Valverius et al. (1987) Mol. Pharmac. 32:217–227.
Charness et al. (1988) Biochem. Biophys. Res. Comm. 155:138–143.
Diamond et al. (1987) Proc. Natl. Acad. Sci. U.S.A. 84:1413–1416.
Dar et al. (1985) Life Sciences 33:P1363–1374.
Dar and Wooles (1986) Life Sciences 39:1429–1437.
Dar et al. (1987) Psychopharmacology 91:1–4.

*Primary Examiner*—Frederick E. Waddell
*Assistant Examiner*—K. E. Weddington
*Attorney, Agent, or Firm*—Townsend and Townsend

[57] ABSTRACT

Alcohol-related disorders are treated by the administration of adenosine antagonists and adenosine agonists to a host. Adenosine antagonists are used to inhibit both acute intoxication and chronic dependence by administering prior to alcohol consumption. The symptoms associated with alcohol withdrawal syndrome may be treated by administering adenosine agonists which reduce the physiological dependence on alcohol during the withdrawal period.

14 Claims, 3 Drawing Sheets

METHODS FOR THE TREATMENT OF ALCOHOL INTOXICATION AND DEPENDENCE

BACKGROUND OF THE INVENTION

1. Field of the Invention

Alcohol intoxication and dependence are serious health problems worldwide. Acute alcohol intoxication can seriously impair an individual's motor function, causing temporary incapacity which exposes the individual and others to potential accidents. Long term alcohol dependence can cause mental and physical disabilities which are detrimental to the individual and society. The problem is exacerbated by physical dependence on the alcohol which results in "alcohol withdrawal syndrome" as the individual ceases alcohol consumption. Alcohol withdrawal syndrome is characterized by tremors, weakness, sweating, hyperflexia, and, in the worst case, delirium tremens.

For these reasons, it would be highly desirable to provide methods to prevent both acute intoxication and long term alcohol dependence as well as for reversing established dependence. It would be particularly desirable if methods could be found which could facilitate withdrawal from long term alcohol dependence by reducing or eliminating the symptoms of alcohol withdrawal syndrome.

2. Description of the Background Art

Ethanol-induced changes in cAMP signal transduction appear to play a role in the acute and chronic effects of ethanol. See, for example, Nagy et al. (1988) Proc. Natl. Acad. Sci. USA 85:6973–6976; Gordon et al. (1986) Proc. Natl. Acad. Sci. USA 83:2105–2108; Valverius et al. (1987) Mol. Pharmac. 32:217–227; and Charness et al. (1988) Biochem. Biophys. Res. Comm. 155:138–143. Ethanol acutely increases receptor-stimulated cAMP levels in NG108-15 neuroblastoma×-glioma hybrids (Gordon et al. (1986) supra.). In contrast, chronic exposure to ethanol causes a decrease in receptor-dependent cAMP levels (Gordon et al. (1986) supra. and Charness et al. (1988) supra.). This reduction appears to be significant in chronic alcoholism since cells from alcoholics exhibit decreases in both adenosine receptor-stimulated and $PGE_1$ receptor-stimulated cAMP levels (Nagy et al. (1988) supra.; and Diamond et al. (1987) Proc. Natl. Acad. Sci USA 84:1413–1416.

Dar et al. have investigated the effects of certain adenosine antagonists (including caffeine, theophylline, and isobutylmethylxanthine on acute and chronic alcohol intoxication. Dar et al. (1985) Life Sciences 33:P1363-1374, set forth that theophylline ameliorated certain symptoms of intoxication while having no effect on others, depending on the time between theophylline administration and ethanol injection. Dipyridamole (which inhibits cellular adenosine uptake) was demonstrated to have a potentiating effect on certain symptoms of ethanol intoxication. Dar and Wooles (1986) Life Sciences 39:1429-1437, describe the effect of administration of caffeine, isobutylmethylxanthine, and theophylline over a 10-day period to mice. The intoxicating effect of ethanol was increased in mice fed isobutylmethylxanthine and caffeine, while theophylline appeared to have no effect. Dar et al. (1987) Psychopharmacology 91:1-4 demonstrates significant potentiation of ethanol-induced ataxia (loss of motor control) in mice pretreated with caffeine, theophylline, and isobutylmethylxanthine.

SUMMARY OF THE INVENTION

Methods for the treatment of alcohol intoxication and withdrawal are provided. Alcohol intoxication is inhibited by the administration of adenosine antagonists to a host prior to consumption of ethanol. Useful antagonists include those specific for the $A_1$ and/or $A_2$ adenosine receptors and, preferably, those which are not transported into the cells and do not inhibit adenosine uptake. In individuals dependent on alcohol or susceptible to such dependence, long term administration of such adenosine antagonists may reverse or inhibit physiological dependence. In addition, the symptoms of alcohol withdrawal syndrome may be reduced by administering adenosine or adenosine agonists to the host. Administration of adenosine or adenosine agonists will reduce physiological dependence on ethanol during the withdrawal period.

DESCRIPTION OF THE SPECIFIC EMBODIMENTS

The following definitions are set forth to illustrate and define the meaning and scope of the various terms used to describe the present invention.

As used herein, the term "host" means a vertebrate host subject to alcohol intoxication and dependence, particularly referring to human hosts. Those individuals dependent on alcohol or susceptible to alcoholism may be identified by biologic tests described in detail in copending application Ser. No. 07/161,628, filed on Feb. 29, 1988, the disclosure of which is incorporated herein by reference. Briefly, basal and receptor-stimulated cAMP levels are measured in freshly isolated lymphocytes, where a reduction in the concentration compared to the expected normal value is diagnostic of alcoholism. Alternatively, an increase in adenosine receptor-stimulated cAMP levels measured in cultured cells not exposed to ethanol compared to the expected normal value is indicative of a predisposition toward alcoholism. Also, decreased adenosine receptor-stimulated cAMP levels in cultured cells from alcoholics exposed to relatively low concentrations of ethanol limited time periods where no decrease in adenosine receptor-stimulated cAMP occurs when normal cultured cells are exposed to ethanol (under the same conditions) is diagnostic of alcoholism susceptibility.

"Adenosine antagonist" refers to an active agent having adenosine receptor blocking activity. Two distinct adenosine receptor classes exist, designated $A_1$ receptors (including subclasses which inhibit adenylate cyclase activity when activated) and $A_2$ receptors which stimulate adenylate cyclase activity when activated. Adenosine antagonists are capable of combining with either or both of these receptors but are incapable of stimulating the normal activity which occurs when adenosine binds to such receptors. As a result, stimulation upon subsequent exposure to adenosine or adenosine agonists will be blocked or inhibited.

Adenosine antagonists suitable for use in the methods of the present invention include those specific or preferential for either or both the $A_1$ and the $A_2$ receptor. Exemplary adenosine antagonists include PD115,199 (an $A_2$ antagonist available from Parke-Davis); 3-(3-hydroxyphenyl)-5H-thiazolo[2,3b]-guinazoline (an $A_2$ antagonist); 1,3-diethyl-8-phenylxanthine and other substituted phenylxanthines ($A_1$ antagonists). Preferred adenosine antagonists according to the present invention are $A_2$ specific, not taken up by the cells to which they bind, and do not inhibit adenosine uptake. Cellular uptake may be measured by techniques described in Aranow and Ullman (1986) J. Biol. Che. 261:2014–2019.

PD 115,199 has the following formula:

PD 115,199 is described in Chemical Abstracts 106:149316x (1987).

As used herein, the term "adenosine agonist" means an active agent capable of combining with either the $A_1$ or $A_2$ receptor and capable of stimulating the associated receptor activity. The term adenosine agonist will also include partial adenosine agonists which are capable of partially stimulating adenosine receptor activity, i.e., providing a lesser activity than would be obtained with a like concentration of adenosine.

Adenosine agonists suitable for use in the methods of the present invention include those specific or preferential for either or both the $A_1$ and the $A_2$ receptor. Exemplary adenosine agonists suitable for use in the methods of the present invention specific for the $A_2$ receptor include CGS21680 (Ciba-Geigy) and 2-phenylaminoadenosine (CV1808). Exemplary adenosine agonists specific for the $A_1$ receptor include N,6-cyclohexyl-adenosine and N,6-cyclopentyladenosine.

Adenosine agonist CGS 21680C has the following formula:

and is described in Chemical Abstracts 112:30385c (1989).

As used herein, the term "treatment" means any administration of the adenosine antagonists or agonists for mediating the effect of short term alcohol exposure or long term alcohol dependence in a vertebrate host, particularly a human, and includes:

(i) inhibiting the symptoms of acute alcohol intoxication;

(ii) lessening or inhibiting the long term effects of alcohol intoxication, including both acute and chronic intoxication; and (iii) relieving the symptoms of alcohol withdrawal.

As used herein, "alcohol" means ethanol.

Administration of the adenosine antagonists and agonists for use in the method of this invention can be via any of the accepted modes of administration. These methods include, but are not limited to, oral, parenteral, transdermal, intraarticular and otherwise systemic administration. Oral administration is preferred. The compounds are administered in a therapeutically effective amount either alone or in combination with a suitable pharmaceutically acceptable carrier or excipient.

Depending on the intended mode of administration, the adenosine antagonist or agonist of choice may be incorporated in any pharmaceutically acceptable dosage form, such as, for example, tablets, transdermal patches, pills, capsules, powders, liquids, suspensions, emulsions, aerosols or the like, preferably in unit dosage forms suitable for single administration of precise dosages, or sustained release dosage forms for continuous controlled administration. Preferably the dosage form will include a pharmaceutically acceptable excipient and, in addition, may contain other medicinal agents, pharmaceutical agents, carriers, adjuvants, etc.

For solid dosage forms, non-toxic carriers include but are not limited to, for example, pharmaceutical grades of mannitol, lactose, starch, magnesium stearate, sodium saccharin, the polyalkylene glycols, talcum, cellulose, glucose, sucrose and magnesium carbonate. Liquid pharmaceutically administrable dosage forms can, for example, comprise a solution or suspension of an active adenosine agent and optional pharmaceutical adjuvants in a carrier, such as, for example, water, saline aqueous dextrose, glycerol, ethanol and the like, to thereby form a solution or suspension. If desired, the pharmaceutical composition to be administered may also contain minor amounts of non-toxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in the art; for example, see Remington's Pharmaceutical Sciences, Mack Publishing Company, Easton, Pa., 16th Edition, 1980. The composition of the formulation to be administered will, in any event, contain a quantity of the active adenosine agent in an amount effective for treatment.

Parenteral administration is generally characterized by injection, either subcutaneously, intramuscularly or intravenously. Injectables can be prepared in conventional forms, either as liquid solutions or suspension, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of active adenosine antagonist or agonist administered will, of course, be dependent on the subject being treated, the severity and nature of the affliction, the manner of administration, the potency and pharmacodynamics of the particular agent and the judgement of the prescribing physician. However, the therapeutically effective dosage for use in this invention will generally be in the range from about 0.01 µg/kg (body weight) to 5 mg/kg.

In treating acute alcohol intoxication, adenosine antagonists will be administered to the host prior to ethanol consumption, usually from about 10 to 60 minutes prior to such consumption, more usually from about 10 to 30 minutes before such consumption. The dosage administered will generally be within the amounts outlined above. By administering the adenosine antagonist prior to ethanol consumption, the acute intoxication effect of the alcohol in the host can be reduced or substantially inhibited.

In treating chronic alcohol dependence, the adenosine antagonists will be administered over a prolonged period, typically for at least one week, more usually being from about 2 to 26 weeks, and frequently the treatment period will be indefinite. The administration will usually be at least daily, more usually being several times a day, although slow release dosage forms may reduce the frequency of administration.

In treating the symptoms of alcohol withdrawal, adenosine agonists will be administered to the host after the consumption of alcohol has ceased and for so long as the host is subject to the symptoms. Typically, the treatment will last for a period of from 3 to 30 days, more typically from about 7 to 21 days, although in some cases the treatment may last indefinitely. The dosage of the agonist will generally be within the amounts outlined above. The administration will be at least daily, more usually being multiple times during the day. Again, slow release dosage forms may find use. The following examples are offered by way of illustration, not by way of limitation.

EXPERIMENTAL

Figure 1:
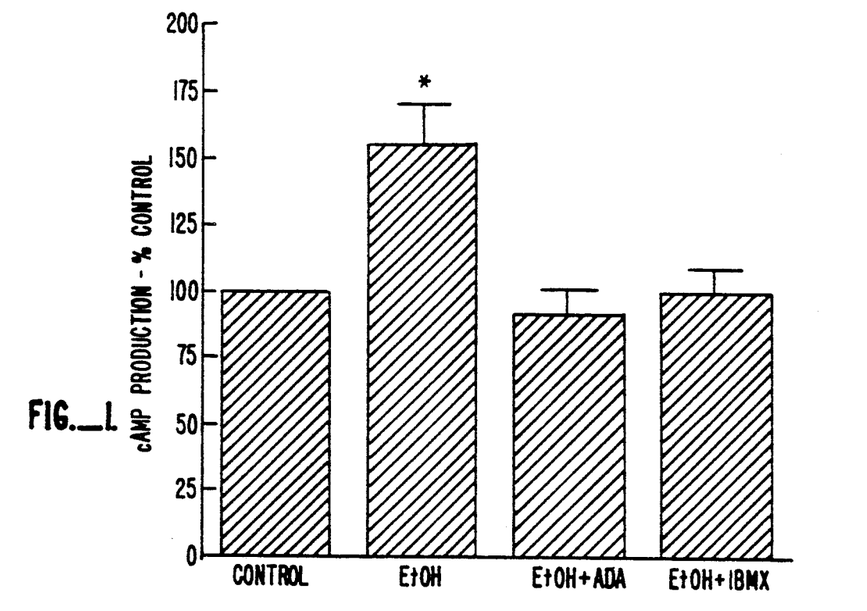
FIG. 1 illustrates the acute effect of ethanol on endogenous cAMP levels in NG108-15 (neuroblastoma×-glioma cells) in the absence of added agonist and phosphodiesterase inhibitors.

NG108-15 cells were grown in defined media as described (Gordon et al. (1986) supra.) to a final density of 12–20×10$^6$ cells per flask. Cells were incubated at 37° C. for 10 min in 9 ml of assay medium containing 100 mM ethanol with or without 1 U/ml adenosine deaminase (ADA) or 10$^{31}$ $^5$M isobutylmethylxanthine (a concentration which blocks adenosine A$_2$ receptors but does not inhibit phosphodiesterase activity) and acetylated cAMP levels determined (Gordon et al. (1986) supra.). The effects of ethanol on cAMP production are illustrated in FIG. 1. Bars represent means ±SEM, n=4–9. The asterisk (*) indicates a significant difference from cells not treated with ethanol (p<0.002, student's t-test). cAMP levels in the absence of ethanol were 18.4±2.4 pmoles/10$^6$ cells (n=16).

Ethanol-induced decreases in receptor-dependent cAMP levels appear to be due to heterologous desensitization of receptors coupled to the stimulatory guanine nucleotide regulatory protein, G$_s$. This desensitization is caused by a decrease in messenger RNA for the α-subunit protein (Mochly-Rosen (1988) Nature 333:848–850). Since heterologous desensitization in other systems is preceded by initial increases in intracellular cAMP (Sibley et al. (1985) Nature 317:124–129), cAMP levels should be increased by treatment with ethanol. When NG108-15 cells were incubated with 200 mM ethanol for 10 min in the absence of added agonist, a 60% increase in intracellular cAMP concentration was observed (FIG. 1). Since ethanol does not directly stimulate adenylate cyclase activity but only receptor-dependent cAMP production (Rabin et al. (1983) J. Pharmac. Exptl. Thera. 227:551–556), the possibility that ethanol increases the extracellular concentration of a stimulatory agonist was considered. Neural cells (Green (1980) Supramol. Structure 13:175–182), lymphocytes (Newby et al. (1981) Biochem. J. 200:399–403; Fredholm et al. (1978) Biochem. Pharmac. 27:2675–2682), and other cell types (Purines: Pharmacology and Physiological Roles, Ed. T. W. Stone, Macmillan Press, Ltd., London, 1985) release adenosine, and adenosine has been implicated in the effects of ethanol (Proctor et al. (1984) Science 224:519–521; Dar et al. (1983) Life Sci. 33:1363–1374). Therefore, adenosine concentrations in the medium of control and ethanol-treated cells were measured using high pressure liquid chromatography (HPLC). The results are shown in FIG. 2.

Figure 2:
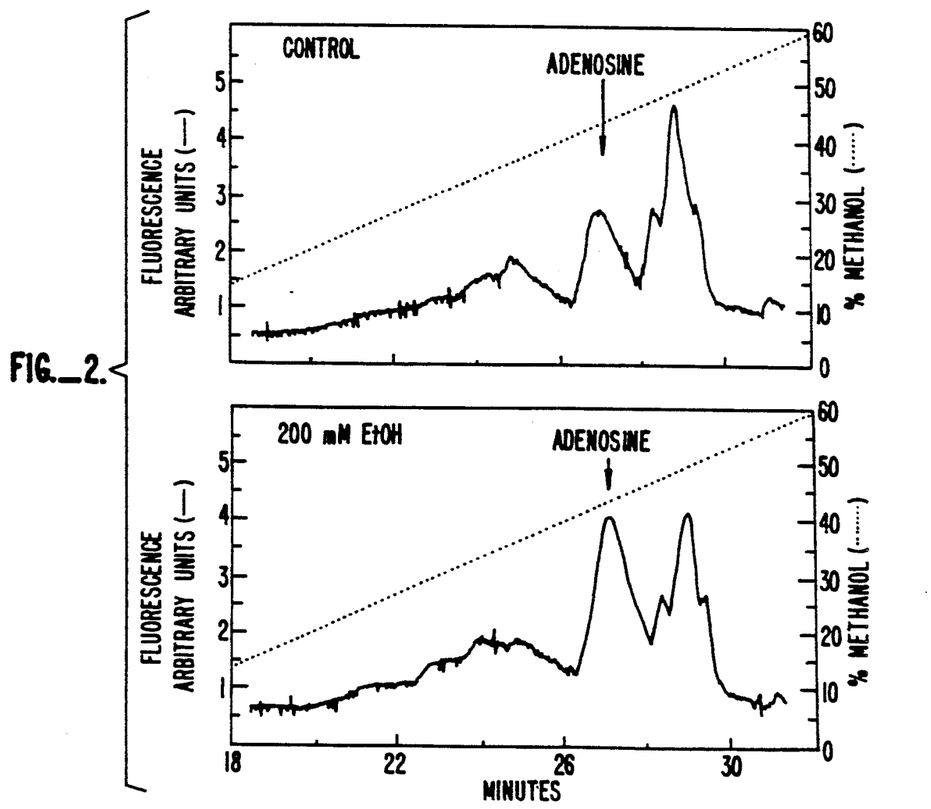
FIG. 2 illustrates the acute effect of ethanol on extracellular adenosine concentration in NG108-15 cells.

Representative chromatograms of control (A) and ethanol-treated cells (B) are shown in FIG. 2. NG108-15 cells (5×10$^6$ cells/well) were incubated with 2 ml of PBS in the presence or absence of 200 mM ethanol for 10 min. Fluorescent derivatives of adenosine were prepared (Green (1980) supra.) and injected onto a reverse-phase HPLC column equilibrated with 1.2 mM KPO$_4$, pH 5 and eluted with a 0–60% methanol gradient. Peak areas were compared with those of known amounts of 1,N$^6$-ethenoadenosine. A significant increase in the concentration of extracellular adenosine was found when NG108-15 cells were incubated with 200 mM ethanol. Within 10 min, adenosine concentrations reached 37±1.2 nM/5×10$^6$ cells in ethanol-treated cells while control cultures had 18.2±3.7 nM adenosine (n=4, p<0.005).

Adenosine stimulates the production of cAMP via the A$_2$ adenosine receptor, which is positively coupled to adenylate cyclase (Daly in: Adv. Cyclic Nucleotides and Protein Phosphorylation (eds. D. M. F. Cooper and K. B. Seamon) Vol. 19, pp. 29–46 (Raven Press, N.Y., 1985). The increase in intracellular cAMP levels produced by acute ethanol (FIG. 1) could therefore be due to activation of adenosine A$_2$ receptors by the extracellular adenosine accumulated in the presence of ethanol. If this were the case, then degradation of extracellular adenosine should prevent stimulation of cAMP production by ethanol. Adenosine deaminase (ADA) was used to deaminate adenosine to inosine, a nucleoside with low affinity for the adenosine receptor. When NG108-15 cells were incubated with ADA, stimulation of cAMP production by ethanol was completely abolished (FIG. 1). Moreover, treatment of the cells with an adenosine receptor antagonist, isobutylmethylxanthine (IBMX), also completely blocked ethanol-induced increases in cAMP levels (FIG. 1). These data suggest that acute exposure to ethanol causes an increase in extracellular adenosine. Accumulated adenosine then binds to the $A_2$ receptor to stimulate cAMP production.

In contrast to the acute stimulation of cAMP levels by ethanol, chronic exposure to ethanol causes a decrease in or desensitization of adenosine receptor and $PGE_1$ receptor-dependent cAMP production (Gordon et al. (1986) supra.; Mochly-Rosen et al. (1988) supra.). If adenosine were responsible for ethanol-induced heterologous desensitization, ADA should prevent this response. The following experiment was performed to test this theory.

Figure 3:
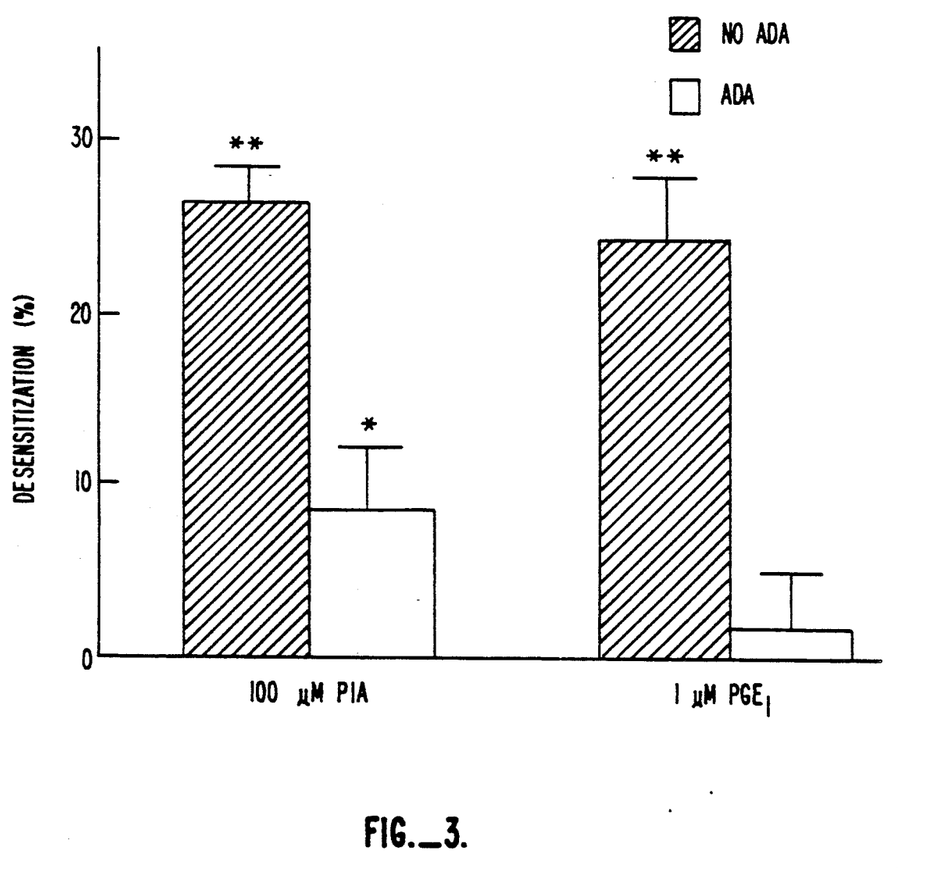
FIG. 3 illustrates the chronic effect of ethanol on desensitization of receptor-stimulated cAMP production in NG108-15 cells.

NG108-15 cells were maintained in 100 mM ethanol for 48 hr with and without 1 U/ml ADA. Adenosine receptor- and $PGE_1$ receptor-stimulated cAMP production were then determined in the absence of ethanol as previously described (Gordon et al. (1986) supra.). In FIG. 3, desensitization is expressed as the percent decrease in ethanol-treated cells compared to cells never exposed to ethanol. ADA was active throughout the incubation period (data not shown). Asterisks indicate a significant difference from cells not treated with ethanol (80-2A6 and 160-D4) were grown in defined media (11, without phytohemagglutinin) with 1 U/ml ADA for at least 2 weeks. They were then grown in the presence or absence of 100 mM ethanol with or without 1.5 U/ml ADA for 48 hours. Accumulation of adenosine over 5 min was determined by incubating $1.0 \times 10^7$ cells/ml in sterilized PBS in the absence or presence of 200 mM ethanol. Extracellular adenosine concentrations were determined as in FIG. 2. Accumulation of adenosine over 24 hours in the absence or presence of 100 mM ethanol was determined as described by Green (1980) supra.. Assays for receptor-stimulated cAMP levels were carried out as in FIG. 3. Basal levels of cAMP were $2.41 \pm 0.28$ pmoles/$10^6$ cells for all cell types and did not change with chronic exposure to ethanol. cAMP levels of ethanol-treated cells are expressed as a percentage of cAMP in cells never exposed to ethanol. Values represent means $\pm$SEM. Number of determinations in indicated in parentheses. The asterisk (*) indicates a significant difference from cells not exposed to ethanol ($p<0.001$). The results are shown in Table 1.

TABLE 1

ADENOSINE TRANSPORT IS REQUIRED FOR ETHANOL-INDUCED HETEROLOGOUS DESENSITIZATION IN S49 CELLS

| Cell Type | EXTRACELLULAR ADENOSINE (nM/$10^7$ cells) | | | | cAMP LEVELS 100 mM EtOH, 48 hr. | |
|---|---|---|---|---|---|---|
| | | No EtOH | | EtOH | 100 uM PIA | 1 uM $PGE_1$ |
| | | | | | (% of control) | |
| Wild Type | 5 min | $4.4 \pm 0.9$ (5) | 200 nM | $17.6 \pm 3.6$ (5) | $65 \pm 7^*$ (27) | $36 \pm 6^*$ (6) |
| | 24 hr. | $21.9 \pm 0.3$ (2) | 100 nM | $56.7 \pm 10.2$ (2) | | |
| Wild Type + Chronic ADA | | ND | | ND | $118 \pm 31$ (4) | $96 \pm 17$ (5) |
| 80-2A6 | 5 min | 0 (2) | 200 mM | 0 (2) | $115 \pm 11$ (6) | $82 \pm 7$ (4) |
| | 24 hr. | 0 (3) | 100 mM | 0 (3) | | |
| 160-D4 | | ND | | ND | $94 \pm 9$ (4) | $98 \pm 7$ (4) |

(*$p<0.025$, **$p<0.001$, student's t-test).

FIG. 3 shows that when NG108-15 cells are co-incubated for 48 hours with ethanol and 1 U/ml ADA, a concentration sufficient to block the acute increase in cAMP (FIG. 1), chronic ethanol-induced desensitization of adenosine receptor-stimulated cAMP levels is substantially blocked and desensitization of the $PGE_1$ receptor is prevented completely.

These results indicate that accumulation of extracellular adenosine is required for the heterologous desensitization produced by chronic exposure to ethanol, as well as for the acute effects of ethanol on cAMP levels. In other preparations, adenosine can cause homologous and heterologous desensitization of receptors (Kenimer et al. (1981) Mol. Pharmac. 20:585-591; Newman et al. (1983) Biochem. Pharmac. 32:137-140); desensitization is dependent on the concentration of agonist and time of exposure (Kenimer et al. (1981) supra.). Consistent with these results, Green (1980) supra., has found in C1300 neuroblastoma cells, that 10-20 nM of endogenously released adenosine is sufficient to desensitize adenosine receptor-dependent cAMP production during an overnight culture.

If accumulation of extracellular adenosine is required for ethanol-induced heterologous desensitization, then cells which do not release adenosine should not desensitize after chronic exposure to ethanol. Adenosine uptake and release are mediated via a single bidirectional transporter which is inactive in the nucleoside transport-deficient mutants 80-2A6 and 160-D4 of the S49 lymphoma cell line. Transport-deficient clones fail to transport adenosine and virtually all other nucleosides. S49 wild type (WT) and adenosine transport mutants Incubation of S49 wild type cells with maximally-effective concentrations of PIA or $PGE_1$ increased cAMP levels $1.92 \pm 0.41$-fold (n=18) and $13.5 \pm 3.5$-fold (n=6) over basal, respectively. Similar results were obtained in the adenosine transport deficient cells (data not shown), indicating that coupling of adenosine receptor and $PGE_1$ receptor to adenylate cyclase is normal in the mutant cells.

S49 wild type cells showed a significant increase in the concentration of extracellular adenosine when exposed to ethanol for 5 min or 24 h (Table 1) but the 80-2A6 mutant cell line failed to accumulate extracellular adenosine under these conditions (Table 1). As expected, when S49 wild type cells were treated with 100 mM ethanol for 48 hours, adenosine receptor and $PGE_1$ receptor-stimulated cAMP levels were reduced to $65 \pm 7$ and $36 \pm 6\%$ of control, respectively (Table 1). As in NG108-15 cells, addition of ADA to S49 wild type cells prevented ethanol-induced heterologous desensitization (Table 1). By contrast, there was no desensitization of adenosine receptor- or $PGE_1$ receptor-stimulated cAMP levels when the adenosine transport-deficient cells were exposed to 100 mM ethanol for 48 hours. (Table 1). Thus, the adenosine transporter is required for ethanol-induced heterologous desensitization of receptor-dependent cAMP production in S49 cells. Although the adenosine transporter is a non-specific nucleoside carrier, other nucleosides have very low affinities for the adenosine receptor and do not stimulate cAMP production (Daly (1985) supra.). In addition, exposure of S49 wild type cells to inosine for 48 hr. did not desensitize the adenosine receptor (data now shown). Taken together these results indicate that accumulation of extracellular adenosine mediates ethanol-induced heterologous desensitization.

Figure 4:
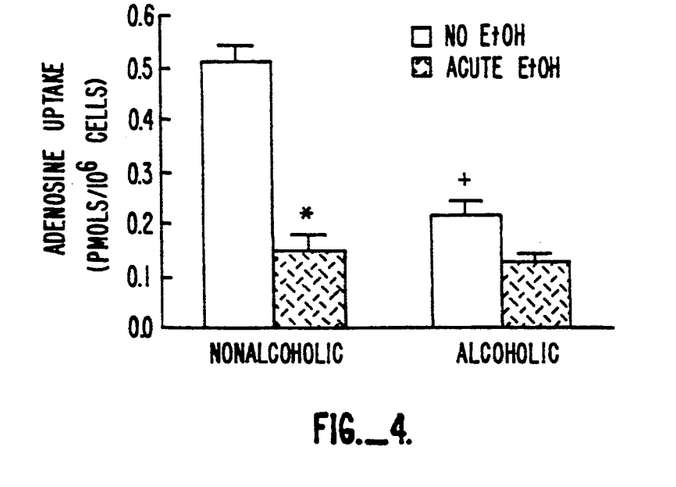
FIG. 4 illustrates the effect of ethanol on adenosine transport in freshly isolated lymphocytes from nonalcoholics and actively drinking alcoholics.

We have noted that in S49 and NG10815 cells, adenosine accumulation is due to inhibition of adenosine uptake after acute ethanol exposure. After chronic exposure to ethanol, acute ethanol no longer inhibits adenosine uptake and consequently no longer causes adenosine accumulation. Uptake of [$^3$H]-adenosine in freshly isolated lymphocytes from nonalcoholics and actively drinking alcoholics was also measured. Lymphocytes were incubated with and without 200 mM ethanol for three minutes, and [$^3$H]-adenosine uptake was measured at 10 seconds. The results are illustrated in FIG. 4. Values represent means ±SEM, n=7 for alcoholics and n=9 for nonalcoholics; *p<0.001 compared to uptake in the absence of ethanol, and +p<0.001 compared to nonalcoholics. Adenosine uptake into freshly-isolated lymphocytes from alcoholics was similar to that observed in S49 cells after chronic exposure to alcohol in that it was relatively insensitive to acute alcohol; there was less inhibition by ethanol compared to uptake in cells from nonalcoholics (FIG. 4). These results indicate that the difference in adenosine uptake in lymphocytes from alcoholics is due at least in part to the effect of in vivo exposure to chronic ethanol on the adenosine transport system.

Lymphocytes from alcoholics and nonalcoholics were grown in culture for 6 days, and 100 mM ethanol was added for 24 hours. The cells were washed, preincubated for 5 minutes in the absence of ethanol, and then incubated in the absence and presence of 100 mM ethanol for 5 minutes. Extracellular adenosine was measured by HPLC (n=5–7 for alcoholics and nonalcoholics). In these experiments, adenosine concentrations in the absence of ethanol did not significantly differ between alcoholics and nonalcoholics (207±26 mM/10$^7$ cells, n=14, including 7 alcoholics and 7 nonalcoholics). *p<0.05, +p<0.025 compared to cells not exposed to ethanol acutely.

Figure 5:
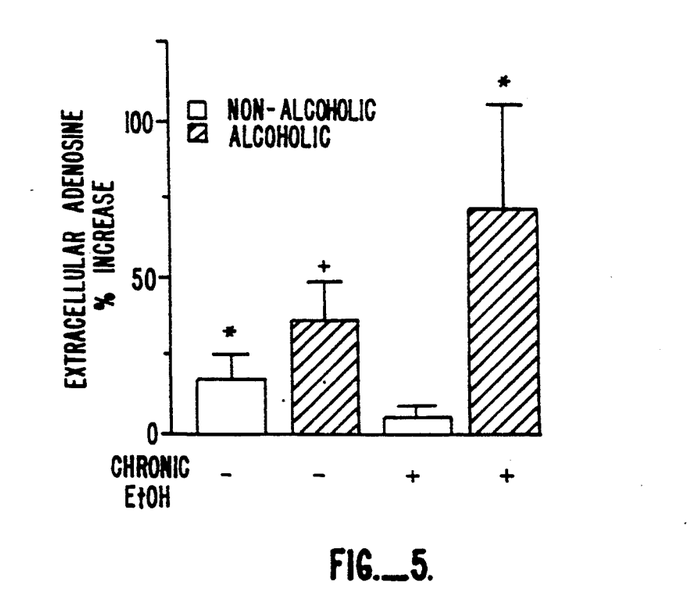
FIG. 5 illustrates the effect of ethanol on extracellular adenosine concentration in cultured lymphocytes from nonalcoholics and actively drinking alcoholics.

Since extracellular adenosine is required for ethanol-induced heterologous desensitization in S49 cells, the effects of ethanol on extracellular adenosine accumulation in cultured lymphocytes from nonalcoholics and alcoholics was investigated. Exposure of lymphocytes from nonalcoholics to 100 mM ethanol for 5 minutes increased the concentration of extracellular adenosine by 17%. In contrast, ethanol increased extracellular adenosine by 37% in lymphocytes from alcoholics (FIG. 5). After chronic exposure to 100 mM ethanol for 24 hours, rechallenge with ethanol did not increase extracellular adenosine in lymphocytes from nonalcoholics. This is similar to results in chronically treated S49 cells. However, cultured lymphocytes from alcoholics, even after chronic exposure to ethanol, still showed a 73% increase in extracellular adenosine when rechallenged with 100 mM ethanol (FIG. 5). Thus, in addition to a greater increase in extracellular adenosine concentration induced by acute ethanol, cells from alcoholics continue to accumulate adenosine even after chronic exposure to ethanol. This appears to account for their increased sensitivity to ethanol-induced heterologous desensitization. These results indicate that administering adenosine antagonists to alcoholics would have even greater therapeutic effects than on nonalcoholics since alcoholics are releasing much larger amounts of adenosine.

In summary, it has been shown that acute exposure to ethanol increases the concentration of extracellular adenosine which then activates adenosine A$_2$ receptors to increase intracellular cAMP levels. Accumulation of extracellular adenosine is also required for the development of chronic ethanol-induced heterologous desensitization of receptor-stimulated cAMP production. Since extracellular adenosine accumulation is greater in alcoholics than nonalcoholics, adenosine antagonist therapy should inhibit the effects of chronic alcohol abuse. Moreover, adenosine agonists should be useful in inhibiting alcohol withdrawal syndrome.

Although the foregoing invention has been described in detail for purposes of clarity of understanding, it will be obvious that certain modifications may be practiced within the scope of the appended claims.

What is claimed is:

1. A method for treating a host suffering from acute ethanol intoxication or chronic ethanol dependence, said method comprising administering an effective amount of on an adenosine antagonist to the host.

2. A method as in claim 1, wherein the adenosine antagonist is administered to the host a predetermined period prior to ethanol consumption in an amount sufficient to inhibit ethanol intoxication.

3. A method as in claim 2, wherein the predetermined period is in the range from about 10 to 60 minutes.

4. A method as in claim 2, wherein the amount of adenosine agonist is in the range from about 0.01 μg/kg (body weight) to 5 mg/kg.

5. A method as in claim 1, wherein the adenosine antagonist is administered periodically to the host in an amount sufficient to inhibit the ethanol dependence.

6. A method as in claim 5, wherein the period of administration is for at least about one week.

7. A method as in claim 5, wherein the amount of adenosine antagonist is in the range from about 0.01 μg/kg (body weight) to 5 mg/kg.

8. A method as in claim 1, wherein the adenosine antagonist is of a type not taken up by the host's cells.

9. A method as in claim 8, wherein the adenosine antagonist is selected from the group consisting of 3-(3-hydroxyphenyl)-5H-thiazolo[2,3b]-guinazoline; 1,3-diethyl-8-phenylxanthine; and

10. A method as in claim 1, wherein the adenosine antagonist is administered orally, parenterally, subcutaneously, or transdermally.

11. A method for treating ethanol withdrawal syndrome in an ethanol-dependent host, said method comprising administering adenosine or an adenosine agonist to the host in an amount sufficient to reduce the symptoms of ethanol withdrawal.

12. A method as in claim 11, wherein the adenosine or adenosine agonist is administered whenever the host is suffering from symptoms of withdrawal.

13. A method as in claim 11, wherein the amount of adenosine or adenosine agonist is in the range from about 0.01 μg/kg (body weight) to 5 mg/kg.

14. A method as in claim 13, wherein the adenosine agonist is selected from the group consisting of N,6-cyclohexyl-adenosine, N,6-cyclopentyladenosine, 2-phenylaminoadenosine, and

* * * * *

UNITED STATES PATENT AND TRADEMARK OFFICE
CERTIFICATE OF CORRECTION

Patent No.: 5,069,895

Dated: December 3, 1991

Inventor(s): Diamond, et al.

It is certified that error appears in the above-identified patent and that said Letters Patent is hereby corrected as shown.

In Column 10, line 29, "adenosine agonist" should read --adenosine antagonist--.

Signed and Sealed this

Eleventh Day of July, 2000

Attest:

Q. TODD DICKINSON

*Attesting Officer*  *Director of Patents and Trademarks*